United States Patent [19]

Neuberger et al.

[11] Patent Number: 5,647,867

[45] Date of Patent: Jul. 15, 1997

[54] LASER ASSISTED DEVICE AND METHOD FOR RESECTOSCOPES

[75] Inventors: Wolfgang Neuberger, Mönchengladbach, Germany; Walter Cecchetti, Padova, Italy; Carol Morello, Palmer, Mass.

[73] Assignee: CeramOptec Industries, Inc., East Longmeadow, Mass.

[21] Appl. No.: 431,260

[22] Filed: Apr. 26, 1995

[51] Int. Cl.⁶ .................................................... A61B 17/36
[52] U.S. Cl. .................... 606/15; 606/39; 606/45
[58] Field of Search .................... 606/14, 15, 16, 606/17, 27, 28, 32, 39, 40, 41, 45, 46, 47, 48, 49, 50, 51

[56] References Cited

U.S. PATENT DOCUMENTS

| | | | |
|---|---|---|---|
| 4,811,733 | 3/1989 | Borsanyi et al. | 606/39 X |
| 4,955,882 | 9/1990 | Hakky . | |
| 5,047,026 | 9/1991 | Rydell | 606/39 X |
| 5,061,266 | 10/1991 | Hakky . | |
| 5,158,561 | 10/1992 | Rydell et al. | 606/39 X |
| 5,190,542 | 3/1993 | Nakao et al. | 606/47 |
| 5,196,007 | 3/1993 | Ellman et al. | 606/32 |
| 5,201,731 | 4/1993 | Hakky . | |
| 5,376,087 | 12/1994 | Haber et al. | 606/27 |
| 5,480,397 | 1/1996 | Eggers et al. | 606/29 |
| 5,540,683 | 7/1996 | Ichikawa et al. | 606/40 |

*Primary Examiner*—Lee S. Cohen
*Assistant Examiner*—Sonya Harris-Ogugua
*Attorney, Agent, or Firm*—Bolesh J. Skutnik

[57] ABSTRACT

A surgical device is provided that is to be used with standardly available resectoscopes, combining the better qualities of familiar tissue scraping tools and real time imaging with the better qualities of laser radiation surgery. The laser radiation is delivered using side-firing optical fibers and is capable of delivering the amount of power needed to ablate or coagulate tissue. The state of the useful art is advanced by incorporating the ability to ablate as well as coagulate tissue using laser radiation, together with the ability to scrape and/or cauterize tissue and simultaneously use familiar real time imaging capabilities, all fitted into a single device that is used with a standard resectoscope. This allows surgeons to use as many familiar and tested techniques as possible and allows hospitals to purchase the device with minimal additional procurement activity. This small and economically packed device will actively promote the surgical use of the best attributes of electromechanical tissue removal devices, laser irradiation devices, and optical imaging devices.

4 Claims, 3 Drawing Sheets

LASER ASSISTED DEVICE AND METHOD FOR RESECTOSCOPES

BACKGROUND OF THE INVENTION

1. Field of the Invention

This invention relates to the field of surgical instruments and methods, specifically to the enhancement of resectoscopes and the applications and more particularly to the addition of a miniature, combined mechanical and photonic means of tissue removal and sampling in surgical applications of standard resectoscopes.

2. Invention Disclosure Statement

A resectoscope is traditionally used transurethrally to perform bladder and/or prostate surgery. The prevailing methods of use of a resectoscope and the devices used during surgery that are inserted through the resectoscope fall in two broad categories, mechanical and laser. The mechanical devices are generally of two types, both using a cutting element formed from thin metal or wire which, after insertion through the resectoscope, are used to remove tissue by scraping. One type is the cold punch type, where the entire device is mechanical. The other has the scraping edge formed with conductive wire, which is heated using electrical current during use. The intent is that the heated element may be used to coagulate blood as well as remove tissue, hopefully reducing bleeding both during the operation and after.

The typical amount of tissue removed during prostate surgery ranges from 20 to 150 grams. A typical single scraping motion using the mechanical devices removes 0.10 grams; it is readily seen that even an ordinary prostate procedure involves 200 or more cutting strokes, producing a time-consuming operation. Although an imaging optical fiber is used in the resectoscope along with the cutting tool, the amount of bleeding that occurs during scraping is such that the surgeon's view is usually cut off by the sheer amount of blood present. During the operation flushing fluid is constantly introduced, flowing from the resectoscope area to the patient's bladder, in an effort to clear the operating area of blood and tissue. The patient's bladder acts as a reservoir for the fluid. Depending upon the amount of bleeding, the patient's bladder must be irrigated at least once during the procedure and possibly more. Additionally, the fluid often cannot dilute the blood to the point of allowing a clear view through the imaging fiber. This creates a situation where surgeons must operate with very limited feedback and with considerable interruptions during the long procedure. Even highly skilled surgeons must maintain conservative distances from other structures in the operating area and cannot tell with precision if they have removed the desired amount of tissue, or are too close and about to intrude into other structures due to the typical variances found between patients.

Pure laser surgery has had limited applicability in this area due to two interrelated problems. One, partially to insure that enough tissue is ablated and partially due to the lack of feedback and control of previous laser implementations, the lased tissue runs deep into the prostate structure and may leave too little healthy tissue, thereby threatening the structural integrity of the prostate. Two, it takes months for the lased tissue to slough off. This means the patient comes out of the operation with the same difficulty as when he entered, and the final results won't be known for months into the future. Due to these unknowns prostate surgery is still commonly executed using traditional scraping techniques, even though laser techniques potentially eliminate the bleeding problem.

Combination surgical tools, using laser and mechanical technologies, have been complex and relatively large and apparently expensive compared to the traditional resectoscope and scrapers. Examples are described by S. I. Hakky in U.S. Pat. Nos. 4,955,882 (Issued Sep. 11, 1990), 5,061,266 (Issued Oct. 29, 1991), and 5,201,731 (Issued Apr. 13, 1993). Such a device, incorporating:

a two-way irrigation system;

a mechanical resection cutter using a blade connected with screws or similar fasteners to a threaded portion of the cutter allowing the blade to be replaced for cost reasons;

a biopsy sample retrieval device using threaded enclosed sections;

an enclosed ultrasonic device; and, imaging and high-power laser delivery systems, must necessarily be considerably more expensive and larger than the tradition resectoscope, and requires the learning of new techniques due to the new method of tissue removal.

BRIEF SUMMARY OF THE INVENTION

It is an aim of the current invention to allow the use of both mechanical and laser devices concurrently or in rapid succession in combination with traditional and readily available resectoscopes.

It is further an aim of the current invention to allow the desirable properties of laser surgery and mechanical surgery to be readily used in conjunction with each other as a surgeon deems necessary during an operation.

It is an additional aim of the current invention to allow the usage of laser surgical devices and techniques while minimizing the overall costs of such laser devices and minimizing the changes to existing equipment, which will facilitate the relatively quick and efficient incorporation of the improved technology into pre-existing material acquisition and cost structures.

It is still a further aim of the current invention to allow a surgeon an easy and straightforward methodological conversion to the use of combined laser and mechanical surgical procedures through the incorporation of both laser and mechanical surgical devices in a single familiar instrument, the traditional resectoscope coupled with a mechanical scraper.

It is another aim of the current invention to readily facilitate the use of a specifically desirable property of laser surgery, ablation and lack of bleeding, with a specifically desirable property of mechanical devices, the immediate removal of tissue, coupled with relatively clear images carried through an imaging optical fiber due to the clarity of the device's liquid immersion as a result of the relative lack of blood, thereby maximizing real time feedback to a surgeon and facilitating accurate removal of tissue.

The above, and other, aims of the invention are realized in the following description and in the embodiments shown in the drawings and the drawings' description.

The invention may be described as having a metallic tube insulated from its surroundings, itself surrounding an optical fiber, which has attached to its distal end two oppositely positioned thin, flexible wires that extend to or past the distal end of the optical fiber. A flexible wire ring connects the distal ends of the two wires, which, when brought past the end of the resectoscope expands outwardly. The metallic tube is connected to a monopolar HF circuit on its proximal end. The fiber's distal end terminates in a side-firing configuration, aimed in a substantially similar direction as that in which the loop expands. The proximal end of the fiber is optically connected to a laser that emits the needed relatively deep coagulation radiation, such as a YAG-type.

In use, the device is extended past the distal end of the resectoscope at which point the loop expands. Laser radiation may now be passed into the prostatic tissue through the side-firing fiber, and the effected tissue removed immediately using the normal sweeping motions of the wire loop. The laser radiation assures ablation or coagulation of the tissue being scraped, and/or of the tissue below that being scraped, thus avoiding most bleeding. If an occasional larger vessel is not completely coagulated, the heated wire loop or the laser may be used to spot-close that particular vessel. This can be done because of the paucity of blood, giving a surgeon the visual acuity to determine the particular spot needing the additional treatment—previous methods made this very specific spot-cauterizing difficult to impossible. In addition to the advantages of immediate removal of tissue and spot cauterizing, the loop, by removing upper layers of ablated, burnt, or coagulated tissue prevents laser radiation from being blocked and therefore allows much finer control of the total energy, and therefore the effective depth, of the ablating or coagulating radiation. This helps avoid the problems of a purely laser-based procedure which requires a deeper ablation/coagulation penetration depth which may lead to the problems related to the leaving of too little healthy tissue in some areas of the prostate, as well as completely avoiding the waiting period associated with that method.

The above, and other objects, features and advantages of the present invention will become apparent from the following description read in conjunction with the accompanying drawings.

DETAILED DESCRIPTION OF THE PREFERRED EMBODIMENT(S)

Figure 1:
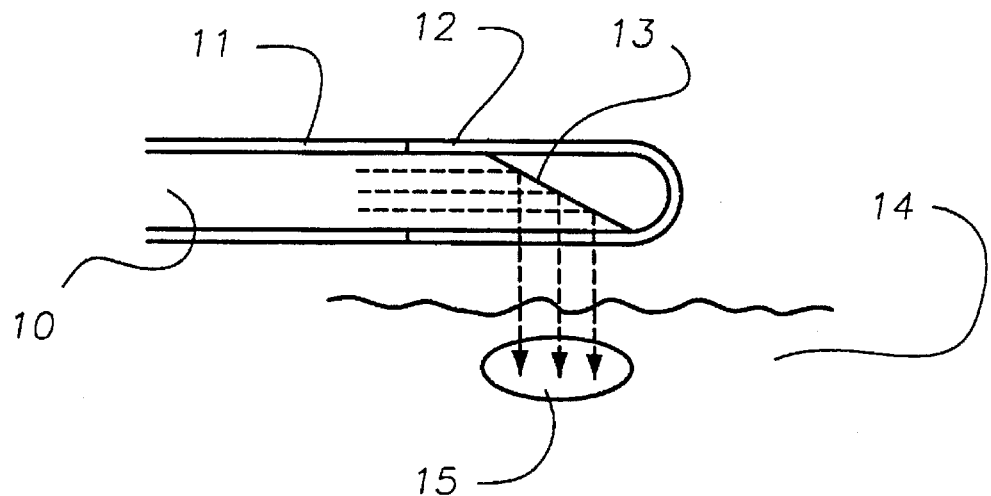
FIG. 1 is a view of a side firing optical fiber that may be used in an embodiment of the invention.
Figure 2:
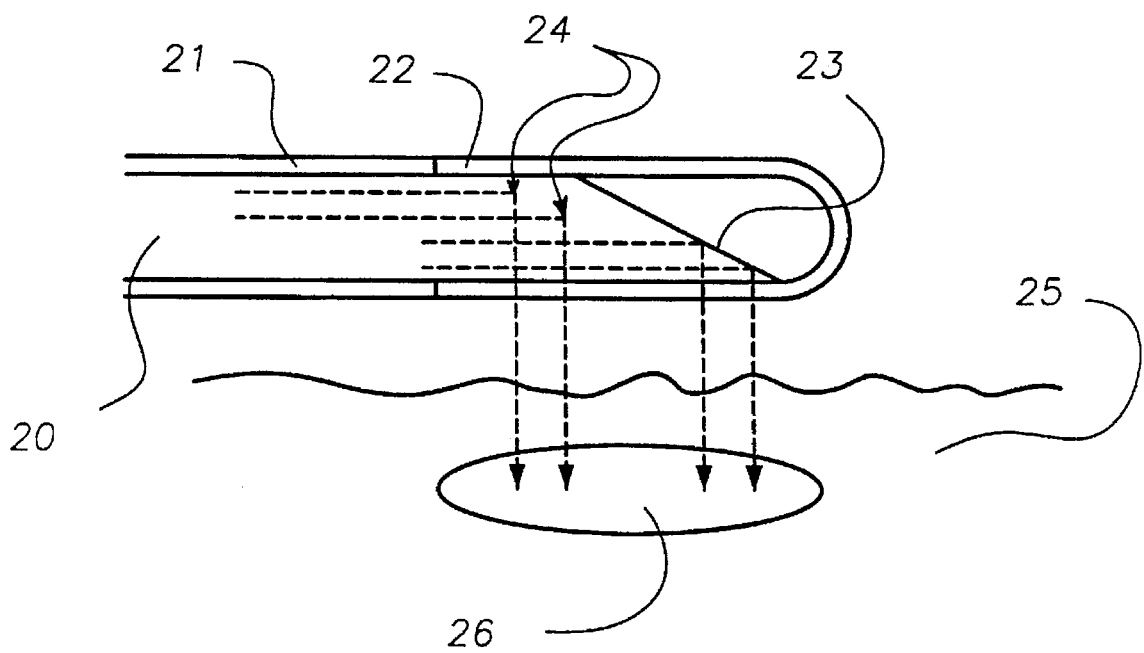
FIG. 2 is a view of a side firing optical fiber with an enlarged ablation/coagulation zone which may be used in the current invention.

Embodiments of the current invention will make use of side-firing optical fiber(s), as illustrated in FIG. 1 and FIG. 2. In FIG. 1, optically conductive fiber 10 is coated with cladding 11 up to the start of quartz tip 12, which both protects optical fiber 10 and allows laser radiation from optical fiber 10 to pass through to tissue 14. Side-firing tip 13 reflects laser radiation travelling parallel to optical fiber 10's longitudinal axis so that the laser radiation now travels in a direction approximately 90 degrees to optical fiber 10's longitudinal axis. Radiation emerging from side-firing tip 13 creates ablated or coagulated tissue area 15, which may be scraped with very minimal bleeding.

FIG. 2 illustrates optically conductive fiber 20 having cladding 21 up to the portion protected with quartz cap 22. In addition to side-firing end 23, directional reflective grooves 24 spread radiation emerging from optical fiber 20 into tissue 25 over coagulated/ablated area 26. Area 26 is significantly larger than the comparable area in FIG. 1, area 15.

Figure 3:
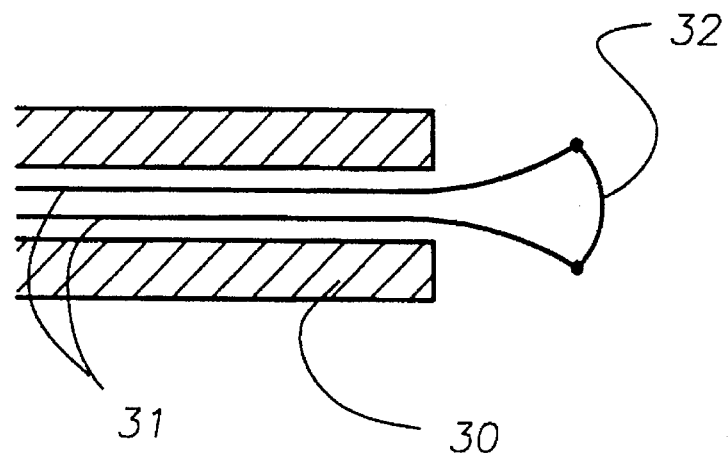
FIG. 3 is a view of a traditional heated loop scraper used with traditional resectoscopes.

FIG. 3 shows a traditional heated loop scraper device emerging from end of resectoscope 30. Wires 31 are conductive and support scraping loop 32. Current is passed through wires 31 during the operation, which heats scraping loop 32. Wires 31, heated scraping loop 32 and resectoscope 30 form the basic traditional heated loop scraping tool.

Figure 4:
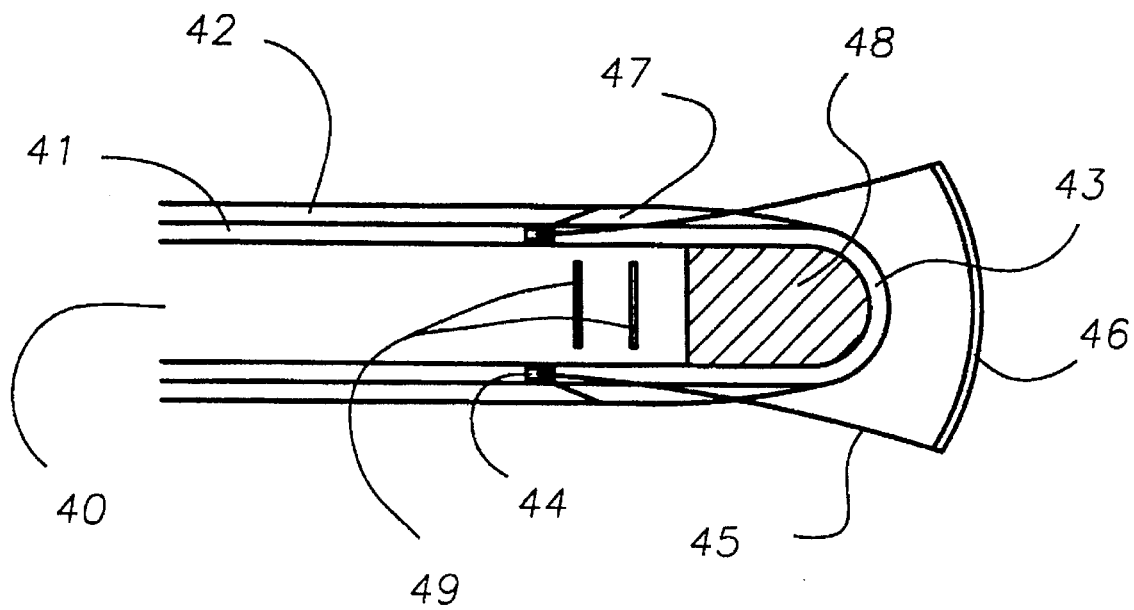
FIG. 4 is a view of one embodiment of the current invention showing the combination of a heated loop scraper and a side firing optical fiber which may be used with a traditional resectoscope.

FIG. 4 shows an embodiment of a combined heated loop scraper and laser radiation delivery device for use with a standard resectoscope. Optical fiber 40 is covered with metallic coating 41, which is covered by insulating coating 42. Metallic coating 41 and insulating coating 42 cover optical fiber 40 until the start of protective quartz cap 43, which covers and protects optical fiber 40 to its end. Metallic coating 41 and scraper wires 45 are rigidly connected at junction 44. The distal ends of scraper wires 45 connect to scraper loop 46. Grooves 47 in quartz cap 43 allow scraper wires 45 and scraper loop 46 to fold in while being passed through a restricted tubular housing to an overall external diameter no greater than the external diameter of insulating coating 42. Optical fiber 40 has side-firing tip 48 and reflection grooves 49 to direct radiation from a laser source to tissue during an operation.

Figure 5:
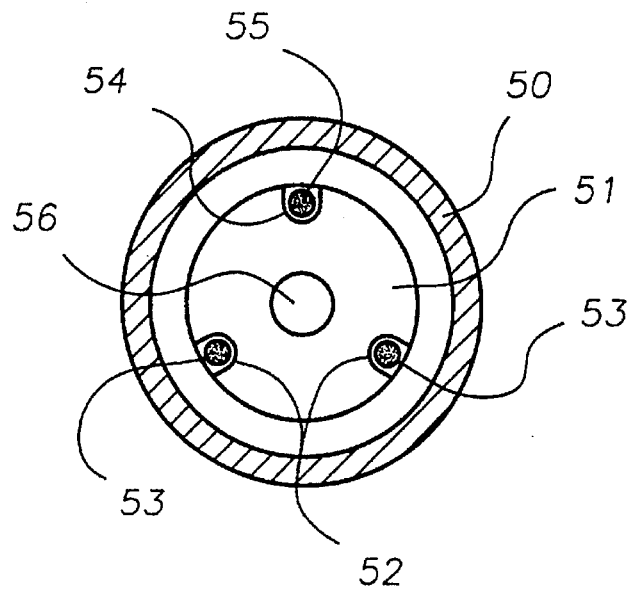
FIG. 5 is a cross-sectional view of an embodiment of the invention similar to FIG. 4, taken near the distal end of the optical fiber and heated loop scraper tools.

FIG. 5 shows a cross section of a preferred embodiment of a combined heated loop scraper and laser delivery device, taken across the distal end of such a device. Quartz cap 51 has grooves 52 that allow scraper wires 53 to fold such that, when scraper wires 53 are folded in during passage through resectoscope 50 the overall outer diameter is no greater than quartz cap 51 alone. Optical fiber 56 is in the center of quartz cap 51. Quartz cap 51 also has passage-way 54 for optical imaging fiber 55.

Figure 6:
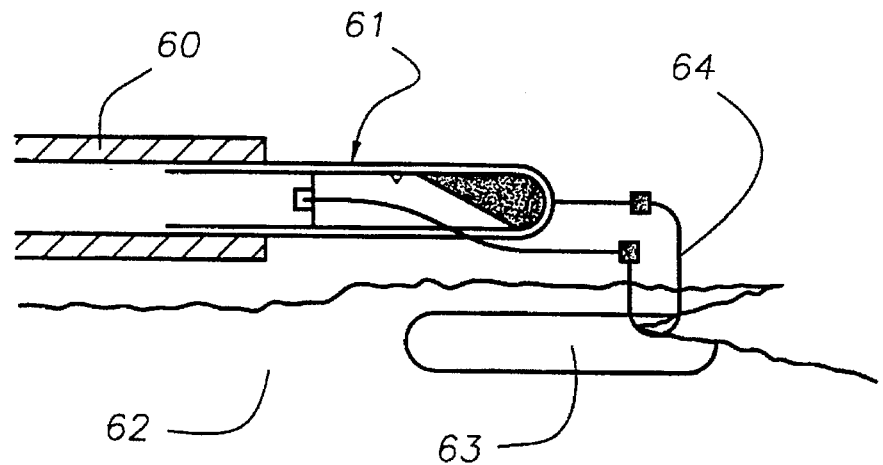
FIG. 6 illustrates a method of use of an embodiment of the invention.

FIG. 6 shows a method of using a combined heated loop scraper and laser deliver device. Heated loop scraper and laser delivery device 61 is extended past the end of resectoscope 60. Radiation from a laser source passes through device 61 and into tissue 62, creating ablation/coagulation area 63. As ablation/coagulation area 63 is being created, device 61 is drawn back towards resectoscope 60. While device 61 is being drawn back leaving ablation/coagulation area 63 behind, scraper loop 64 removes any tissue above ablated/coagulated tissue 63 as well as most of ablated/coagulated tissue 63. Because tissue in and above area 63 is ablated or coagulated, bleeding is eliminated or significantly and substantially reduced, and lazed tissue is removed immediately so the body need not sluff it off over a period of months.

Figure 7:
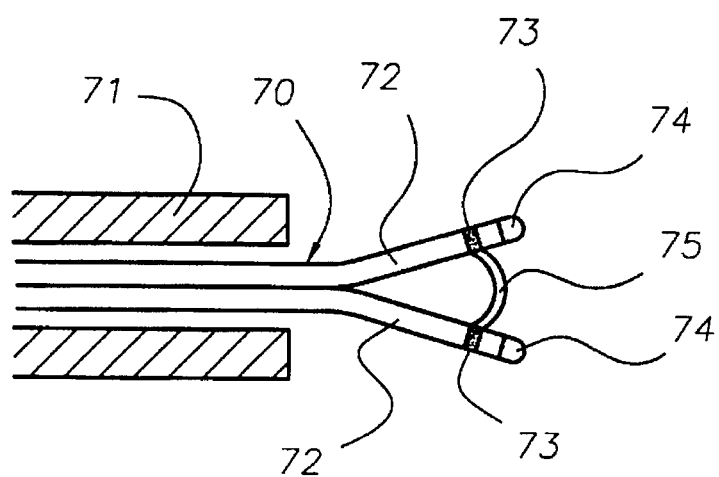
FIG. 7 is a view of a two side firing optical fiber embodiment of the current invention.

FIG. 7 shows an embodiment where heated loop scraper and laser radiation delivery device 70, shown extended past the distal end of standard resectoscope 71, has two side-firing optical fibers 72 coated with metallic and insulating sheaths extending along optical fibers 72 to attachment points 73. Heated scraper loop 75 is rigidly connected to attachment points 73. Side-firing optical fiber tips 74 pass laser radiation to points below and slightly back towards resectoscope 71. The optical fiber itself may be fixed, movable, partially movable or alternatively movable relative to the heated loop scraper.

In one preferred embodiment, the inner channel of a metallic tube delivering the current has a non-circular cross-section matching the non-circular cross-section of the fiber coating thus inhibiting relative rotation of the two components, yet allowing relative axial displacement. This radial axial displacement may be activated by a squeeze connector affixed to the metallic tube that can be in firm contact with the fiber's coating so as to fix them relative to each other.

In another preferred embodiment, a bipolar HF circuit may be used instead of the monopolar circuit described above. In this embodiment, two insulated wires are embedded in a fixed or movable manner in the sheath of the optical fiber. The two wires are connected to a loop near the output end of the fiber.

Having described preferred embodiments of the invention with references to the accompanying drawings, it is to be understood that the invention is not limited to that precise embodiment and that various changes and modifications may be effected therein by one skilled in the art without departing from the scope or spirit of the invention as defined in the appended claims.

What is claimed is:

1. A medical device for use with standardly available resectoscopes which have distal and proximal ends and have at least one channel within said resectoscopes and where said resectoscope's distal end may be introduced into a living body and be positioned near an organ on which surgery is to be performed; said medical device comprising:

an elongated shape, having a distal end and a proximal end;

means for tissue removal;

means for laser radiation delivery from said device's proximal end to said device's distal end;

said means for tissue removal and said means for laser radiation delivery concurrently lying within said device's elongated shape and wherein said radiation delivery means and said tissue removal means may operate independently, sequentially or concurrently on said organ undergoing surgery;

said means for laser radiation delivery further comprises; an optical fiber having a proximal and a distal end; said proximal end being optically connected to a laser radiation source; and said distal end comprising a side firing tip to deliver said laser radiation to an area positioned substantially perpendicular to a longitudinal axis of said optical fiber; and said distal end having an outside diameter in the range of about 1.0 mm to about 2.8 mm, such that said device's distal end can enter and pass freely through a channel within said standardly available resectoscope.

2. The medical device according to claim 1, wherein said means for tissue removal is an electrochemical means further comprising:

a conductive loop with two ends;

first and second conductive wires running substantially parallel to a major axis of said device's elongated shape;

each of said conductive wires extending beyond said device's distal and proximal ends;

an end of said conductive loop being substantially rigidly connected to a distal end of said first conductive wire and another loop end being substantially rigidly connected to a distal end of a second conductive wire;

proximal ends of said conductive wires being connected to an electrical power source; and said electrochemical means being inserted in said device through said resectoscope concurrently with said means for laser radiation delivery.

3. The device according to claim 1, wherein said means for tissue removal is an electrochemical means which further comprises; a conductive loop with two ends, first and second conductive wires running substantially parallel to a major axis of said device's elongated shape, each of said conductive wires extending beyond said device's distal and proximal ends, an end of said conductive loop being substantially rigidly connected to a distal end of said first conductive wire and another loop end being substantially rigidly connected to a distal end of a second conductive wire, and proximal ends of said conductive wires being connected to an electrical power source; and said optical fiber being concurrently inserted through said resectoscope with said two conductive wires.

4. A method for doing one of ablating or coagulating tissue and removing said tissue on a living being, said method comprising the steps of:

inserting a standard resectoscope having a proximal and a distal end into a living body such that said distal end is located near an area where said tissue removal is required;

inserting through a channel in said standard resectoscope a device having both means for electrochemically removing tissue and means for laser radiation delivery;

utilizing said means for laser radiation delivery either to ablate or coagulate said tissue to be removed by controlling power output from a laser radiation source and by moving said means for laser radiation delivery across an area of tissue to be treated;

wherein said means for laser radiation delivery further comprises; an optical fiber having a proximal and a distal end; said proximal end being optically connected to a laser radiation source; and said distal end comprising a side firing tip to deliver said laser radiation to an area positioned substantially perpendicular to a longitudinal axis of said optical fiber;

utilizing said means for electrochemically removing tissue to remove irradiated tissue by passing said means for removing essentially over said area to irradiated tissue; and operating said means for laser radiation delivery and said means for electrochemically removing tissue in one of two ways, concurrently or in succession without having to remove either means from said resectoscope.

* * * * *